(12) United States Patent
Zhou et al.

(10) Patent No.: US 8,981,164 B2
(45) Date of Patent: Mar. 17, 2015

(54) COBALT AND TIN HYDROGENATION CATALYSTS

(71) Applicant: Celanese International Corporation, Irving, TX (US)

(72) Inventors: Zhenhua Zhou, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 132 days.

(21) Appl. No.: 13/722,038

(22) Filed: Dec. 20, 2012

(65) Prior Publication Data

US 2013/0178669 A1 Jul. 11, 2013

Related U.S. Application Data

(63) Continuation-in-part of application No. 13/595,365, filed on Aug. 27, 2012.

(60) Provisional application No. 61/583,874, filed on Jan. 6, 2012.

(51) Int. Cl.
| | | |
|---|---|---|
| C07C 27/04 | (2006.01) | |
| C07C 29/153 | (2006.01) | |
| B01J 37/02 | (2006.01) | |
| B01J 23/94 | (2006.01) | |
| B01J 23/00 | (2006.01) | |
| B01J 23/89 | (2006.01) | |
| B01J 37/18 | (2006.01) | |
| B01J 23/888 | (2006.01) | |
| B01J 37/00 | (2006.01) | |

(52) U.S. Cl.
CPC ........... *C07C 29/153* (2013.01); *B01J 37/0205* (2013.01); *B01J 23/94* (2013.01); *B01J 23/002* (2013.01); *B01J 23/898* (2013.01); *B01J 23/8986* (2013.01); *B01J 23/8993* (2013.01); *B01J 2523/00* (2013.01); *B01J 37/18* (2013.01); *B01J 23/888* (2013.01); *B01J 37/0018* (2013.01)
USPC ........................................................ 568/885

(58) Field of Classification Search
CPC .................................................. C07C 29/153
USPC ........................................................ 568/885
See application file for complete search history.

(56) References Cited

U.S. PATENT DOCUMENTS

| | | | |
|---|---|---|---|
| 2,549,416 A | 4/1951 | Brooks | |
| 2,607,807 A | 8/1952 | Ford | |
| 3,361,769 A | 1/1968 | Halpern et al. | |
| 3,478,112 A | 11/1969 | Karl et al. | |
| 3,531,543 A | 9/1970 | Clippinger et al. | |
| 3,864,284 A | 2/1975 | Clippinger et al. | |
| 3,953,524 A | 4/1976 | Steiner | |
| 3,981,923 A | 9/1976 | Stouthamer et al. | |
| 4,199,438 A | 4/1980 | Antos | |
| 4,317,918 A | 3/1982 | Takano et al. | |
| 4,337,351 A | 6/1982 | Larkins, Jr. | |
| 4,374,265 A | 2/1983 | Larkins, Jr. | |
| 4,398,039 A * | 8/1983 | Pesa et al. ..................... 560/265 |
| 4,426,541 A | 1/1984 | King | |
| 4,456,775 A | 6/1984 | Travers et al. | |
| 4,476,326 A | 10/1984 | Lin et al. | |
| 4,480,115 A | 10/1984 | McGinnis | |
| 4,514,515 A | 4/1985 | Travers et al. | |
| 4,514,521 A | 4/1985 | Smith | |
| 4,517,391 A | 5/1985 | Schuster et al. | |
| 4,550,185 A | 10/1985 | Mabry et al. | |
| 4,628,130 A | 12/1986 | Bournonville et al. | |
| 4,760,171 A | 7/1988 | Isogai et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,837,368 A | 6/1989 | Gustafson et al. | |
| 4,880,937 A | 11/1989 | Matsushita et al. | |
| 4,985,572 A | 1/1991 | Kitson et al. | |
| 4,990,655 A | 2/1991 | Kitson et al. | |
| 5,008,235 A | 4/1991 | Wegman et al. | |
| 5,061,671 A | 10/1991 | Kitson et al. | |
| 5,137,861 A | 8/1992 | Shih et al. | |
| 5,149,680 A * | 9/1992 | Kitson et al. .................. 502/185 |
| 5,155,084 A | 10/1992 | Horn et al. | |
| 5,185,476 A | 2/1993 | Gustafson | |
| 5,243,095 A | 9/1993 | Roberts et al. | |
| 5,292,704 A | 3/1994 | Lester | |
| 5,292,916 A | 3/1994 | Matsuzaki et al. | |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Fereydoun G Sajjadi
*Assistant Examiner* — Kofi Adzamli

(57) ABSTRACT

The present invention relates to catalysts, to processes for making catalysts and to chemical processes employing such catalysts. The catalysts are preferably used for converting acetic acid and ethyl acetate to ethanol. The catalyst comprises a precious metal, tin and cobalt, wherein molar ratio of cobalt to tin is at least 11:1.

20 Claims, 1 Drawing Sheet

(56) References Cited

U.S. PATENT DOCUMENTS

| | | | |
|---|---|---|---|
| 5,334,769 A | 8/1994 | Ferrero et al. |
| 5,350,504 A | 9/1994 | Dessau |
| 5,391,291 A | 2/1995 | Winquist et al. |
| 5,426,246 A | 6/1995 | Nagahara et al. |
| 5,476,827 A | 12/1995 | Ferrero et al. |
| 5,585,523 A | 12/1996 | Weiguny et al. |
| 5,719,097 A | 2/1998 | Chang et al. |
| 5,767,307 A | 6/1998 | Ramprasad et al. |
| 5,849,657 A | 12/1998 | Rotgerink et al. |
| 5,945,570 A | 8/1999 | Arhancet et al. |
| 5,955,397 A | 9/1999 | Didillon et al. |
| 5,977,010 A | 11/1999 | Roberts et al. |
| 6,046,127 A | 4/2000 | Mimoun |
| 6,121,498 A | 9/2000 | Tustin et al. |
| 6,204,417 B1 | 3/2001 | Fisher et al. |
| 6,281,160 B1 | 8/2001 | Basset et al. |
| 6,294,703 B1 | 9/2001 | Hara et al. |
| 6,414,209 B1 | 7/2002 | Herskowitz et al. |
| 6,462,244 B1 | 10/2002 | Huang et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,524,993 B2 | 2/2003 | Yamaguchi et al. |
| 6,559,333 B1 | 5/2003 | Brunelle et al. |
| 6,670,490 B1 | 12/2003 | Campos et al. |
| 6,903,045 B2 | 6/2005 | Zoeller et al. |
| 6,906,228 B2 | 6/2005 | Fischer et al. |
| 7,084,312 B1 | 8/2006 | Huber et al. |
| 7,335,800 B2 | 2/2008 | Komplin et al. |
| 7,375,049 B2 | 5/2008 | Hayes et al. |
| 7,425,657 B1 | 9/2008 | Elliott et al. |
| 7,538,060 B2 | 5/2009 | Barnicki et al. |
| 7,790,938 B2 | 9/2010 | Kawasaki et al. |
| 7,842,844 B2 | 11/2010 | Atkins |
| 7,847,134 B2 | 12/2010 | Lee et al. |
| 7,884,253 B2 | 2/2011 | Stites et al. |
| 7,923,405 B2 | 4/2011 | Kharas et al. |
| 7,964,379 B2 | 6/2011 | Verser et al. |
| 8,071,389 B2 | 12/2011 | Weck et al. |
| 8,080,694 B2 | 12/2011 | Weiner et al. |
| 8,173,324 B2 | 5/2012 | Fisher et al. |
| 8,232,440 B2 | 7/2012 | Holtzapple et al. |
| 8,288,596 B2 | 10/2012 | Garton et al. |
| 8,309,782 B2 | 11/2012 | Le Peltier et al. |
| 8,329,961 B2 | 12/2012 | Danjo et al. |
| 2003/0105171 A1 | 6/2003 | Subramanian et al. |
| 2006/0102520 A1 | 5/2006 | Lapinski et al. |
| 2006/0241325 A1 | 10/2006 | Komplin et al. |
| 2007/0238605 A1 | 10/2007 | Strehlau et al. |
| 2008/0207953 A1 | 8/2008 | Houssin et al. |
| 2008/0227627 A1 | 9/2008 | Strehlau et al. |
| 2008/0257784 A1 | 10/2008 | Dath et al. |
| 2010/0029996 A1 | 2/2010 | Danjo et al. |
| 2010/0121114 A1 | 5/2010 | Johnston et al. |
| 2010/0197486 A1 | 8/2010 | Johnston et al. |
| 2010/0249479 A1 | 9/2010 | Berg-Slot et al. |
| 2011/0046421 A1 | 2/2011 | Daniel et al. |
| 2011/0060169 A1 | 3/2011 | Kaizik et al. |
| 2011/0190117 A1 | 8/2011 | Weiner et al. |
| 2012/0209034 A1 | 8/2012 | Zhou et al. |
| 2012/0238785 A1 | 9/2012 | Zhou et al. |

FOREIGN PATENT DOCUMENTS

| | | |
|---|---|---|
| CN | 102229520 | 11/2011 |
| EP | 0104197 | 4/1984 |
| EP | 0175558 | 3/1986 |
| EP | 0192587 | 8/1986 |
| EP | 0400904 | 5/1990 |
| EP | 0372847 | 6/1990 |
| EP | 372847 A2 * | 6/1990 |
| EP | 0408528 | 7/1990 |
| EP | 0653242 | 5/1995 |
| EP | 1074299 | 2/2001 |
| EP | 2060553 | 5/2009 |
| FR | 2524339 | 10/1983 |
| GB | 1559540 | 1/1980 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 2007/107371 | 9/2007 |
| WO | WO 2009/009322 | 1/2009 |
| WO | WO 2011/053367 | 5/2011 |

OTHER PUBLICATIONS

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

International Search Report and Written Opinion mailed Apr. 29, 2013 in corresponding International Application No. PCT/US2012/070947.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

\* cited by examiner

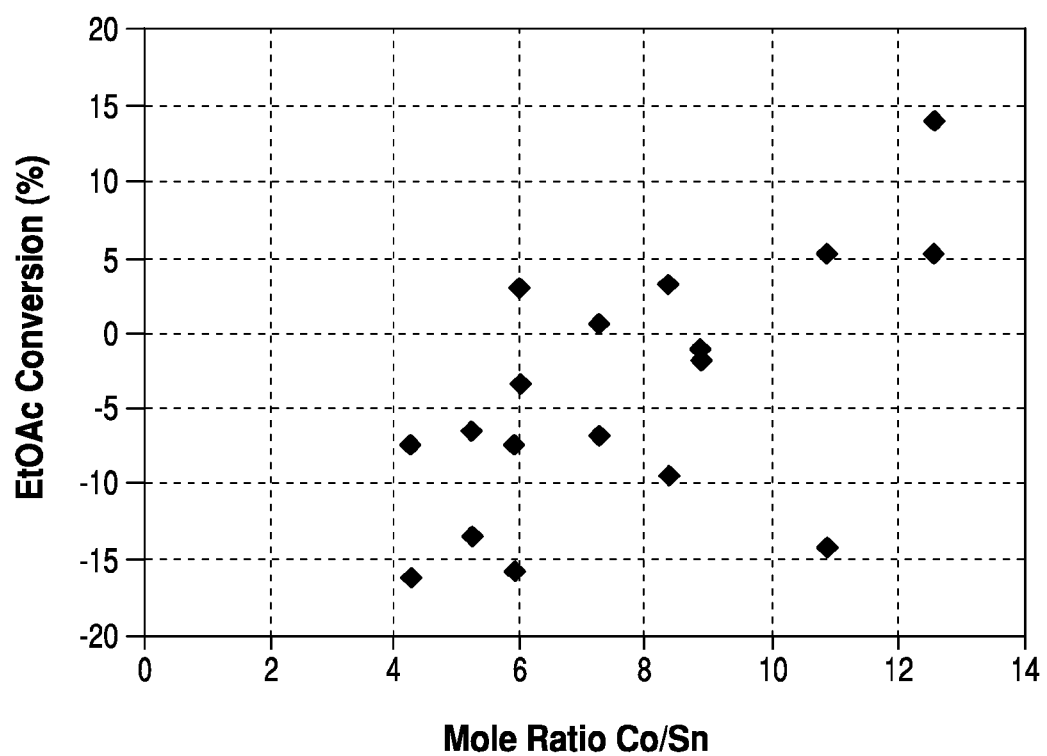

COBALT AND TIN HYDROGENATION CATALYSTS

CROSS REFERENCE TO RELATED APPLICATION

This application is a continuation-in-part of U.S. application Ser. No. 13/595,365, filed Aug. 27, 2012, which claims priority to U.S. Provisional App. No. 61/583,874, filed on Jan. 6, 2012, the entirety of which is incorporated herein by reference.

FIELD OF THE INVENTION

The present invention relates to catalysts comprising a precious metal, cobalt and tin and to processes for producing ethanol from a feed stream comprising a carboxylic acid and/or esters thereof in the presence of the inventive catalysts.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis,* 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; (iv) insufficient catalyst life; and/or (v) required activity for both ethyl acetate and acetic acid.

SUMMARY OF THE INVENTION

In a first embodiment, the invention is directed to a catalyst on a modified support, comprising a precious metal, tin and cobalt, wherein the modified support comprises a support modifier metal selected from the group consisting of tungsten, molybdenum, vanadium, niobium, and tantalum, and further wherein a molar ratio of cobalt to tin is at least 11:1. The precious metal may be selected from the group consisting of rhodium, rhenium, ruthenium, platinum, palladium, osmium, iridium and gold. The catalyst may further comprise a second metal selected from the group consisting of copper, iron, vanadium, nickel, titanium, zinc, chromium, molybdenum, tungsten, lanthanum, cerium, and manganese. The precious metal may be present in an amount from 0.1 to 5 wt. %, the tin may be present in an amount from 0.05 to 4.5 wt. % and the cobalt may be present in an amount from 3 to 25 wt. %, based on the total weight of the catalyst. In some embodiments, the support modifier metal is tungsten. In some embodiments, the modified support further comprises cobalt, tin, or mixtures thereof. The catalyst and/or modified support may be free of tin tingstate. There may be an excess molar amount of tin compared to the precious metal in the catalyst. The modified support may comprise a support material selected from the group consisting of silica, alumina, titania, silica/alumina, pyrogenic silica, high purity silica, zirconia, carbon, zeolites and mixtures thereof.

In a second embodiment, the present invention is directed to a process for producing ethanol, comprising contacting a feedstock comprising acetic acid and hydrogen in a reactor at an elevated temperature in the presence of a catalyst, under conditions effective to form ethanol, wherein the catalyst is on a modified support, the catalyst comprising a precious metal, tin and cobalt, wherein the modified support comprises a support modifier metal selected from the group consisting of tungsten, molybdenum, vanadium, niobium, and tantalum, and further wherein a molar ratio of cobalt to tin is at least 11:1. The feed stream may further comprise ethyl acetate and the ethyl acetate conversion may be at least 5%. Acetic acid conversion may be at least 75% with a selectivity to ethanol of greater than 80%. The hydrogenation may be performed in a vapor phase at a temperature of from 125° C. to 350° C., a pressure of 10 kPa to 3000 kPa, and a hydrogen to acetic acid molar ratio of greater than 4:1. The acetic acid is derived from a carbonaceous material selected from the group consisting of oil, coal, natural gas and biomass.

In a third embodiment, the present invention is directed to a catalyst on a modified support, comprising a precious metal and tin, wherein the modified support comprises cobalt and a support modifier metal selected from the group consisting of tungsten, molybdenum, vanadium, niobium, and tantalum; and further wherein the molar ratio of cobalt to tin is at least 11:1. The precious metal may be selected from the group consisting of rhodium, rhenium, ruthenium, platinum, palladium, osmium, iridium and gold. The catalyst may further comprise a second metal that is selected from the group consisting of copper, iron, vanadium, nickel, titanium, zinc, chromium, molybdenum, tungsten, lanthanum, cerium, and manganese.

In a fourth embodiment, the present invention is directed to a catalyst on a modified support, comprising a precious metal, tin and cobalt, wherein the modified support comprises a support modifier metal selected from the group consisting of tungsten, molybdenum, vanadium, niobium, and tantalum; and further wherein the molar ratio of cobalt to tin is at least 11:1. The precious metal may be selected from the group consisting of rhodium, rhenium, ruthenium, platinum, palladium, osmium, iridium and gold.

BRIEF DESCRIPTION OF THE DRAWINGS

The present invention will be better understood in view of the appended non-limiting FIGURE, in which:

FIG. 1 is a chart showing ethyl acetate conversion at varied cobalt/tin molar ratios.

DETAILED DESCRIPTION OF THE INVENTION

Catalyst Composition

The present invention is directed to catalyst compositions that preferably are suitable as hydrogenation catalysts and to chemical processes employing such catalysts. The catalysts preferably comprise a precious metal, tin, and cobalt on a support, preferably a modified support, and may be suitable in catalyzing the hydrogenation of a carboxylic acid, e.g., acetic acid, and esters thereof, e.g., ethyl acetate, to the corresponding alcohol, e.g., ethanol. The cobalt and tin may be present as metals on the modified support and/or may be formed with the support modifier metals on the support material to form the modified support.

In one embodiment, the inventive catalyst comprises a precious metal, cobalt and tin on a modified support. The molar ratio of cobalt to tin is at least 11:1, e.g. at least 11.5:1, at least 12:1, or at least 13:1. The molar excess of cobalt is advantageous to converting both carboxylic acids, such as acetic acid, and esters thereof, e.g., ethyl acetate, to their corresponding alcohol(s), e.g., ethanol, under hydrogenation conditions. In addition, the amount of tin needed for the catalyst may be decreased by increasing the cobalt loadings. The catalysts of the present invention having the molar excess of cobalt may have an acetic acid conversion greater than 75%, e.g., greater than 80%, greater than 90%, or greater than 95%, and an ethyl acetate conversion greater than greater than 5%, e.g., greater than 10%. Lower ethyl acetate conversions, including negative ethyl acetate conversion, are not suitable for converting both acetic acid and ethyl acetate. A negative conversion indicates that there is a net increase in ethyl acetate from the amount of ethyl acetate in the feed stream to the amount of ethyl acetate in the crude ethanol product.

In one embodiment, the catalyst may comprise cobalt in an amount from 3 to 25 wt. %, e.g., preferably from 5 to 25 wt. % or from 5 to 20 wt. %, and tin in an amount from 0.05 to 4.5 wt. %, e.g., preferably from 0.1 to 4 wt. % or from 0.5 to 3 wt. %. For purposes of the present specification, unless otherwise indicated, weight percent is based on the total weight the catalyst including metal and support.

In some embodiments, the catalyst may comprise cobalt and/or tin disposed on the modified support and as part of the modified support. The molar ratio is calculated based on the total amount of cobalt and tin in the overall catalyst, including both as disposed on the modified support and as part of the modified support. In one embodiment, the modified support also comprises cobalt and/or tin. Without being bound by theory, cobalt and/or tin when part of the modified support may be dispersed the support modifier metal or oxide thereof on the support. Cobalt and/or tin are part of the modified support when it is impregnated and calcined on the support material prior to the impregnation or introduction of the precious metal to the modified support.

The modified support may comprise a support modifier metal selected from the group consisting of tungsten, molybdenum, vanadium, niobium and tantalum. In one aspect, the modified support comprises cobalt and/or tin and cobalt and/or tin are also disposed on the support. A support modifier metal, along with any cobalt and/or tin, may adjust the acidity of the support material. The metal for the support modifier may be an oxide thereof. In one embodiment, the support modifier metals are present in an amount from 0.1 wt. % to 50 wt. %, e.g., from 0.2 wt. % to 25 wt. %, from 0.5 wt. % to 20 wt. %, or from 1 wt. % to 15 wt. %, based on the total weight of the catalyst. When the support modifier comprises tungsten, molybdenum, and vanadium, the support modifier may be present in an amount from 0.1 to 40 wt. %, e.g., from 0.1 to 30 wt. % or from 0.1 to 20 wt. %, based on the total weight of the catalyst. In one embodiment, a higher loading of the support modifier metal may also improve ethyl acetate conversion. For example, when the support modifier metal is present in an amount of greater than 14 wt. %, e.g., greater than 15 wt. %, and the molar ratio of cobalt to tin is greater than 11:1 the ethyl acetate conversion may be more than 5 wt. %.

The catalysts of the invention preferably include at least one precious metal impregnated on the modified support. The precious metal may be selected, for example, from rhodium, rhenium, ruthenium, platinum, palladium, osmium, iridium and gold. Preferred precious metals for the catalysts of the invention include palladium, platinum, and rhodium. The precious metal preferably is catalytically active in the hydrogenation of a carboxylic acid and/or its ester to the corresponding alcohol(s). The precious metal may be in elemental form or in molecular form, e.g., an oxide of the precious metal. The catalyst comprises such precious metals in an amount less than 5 wt. %, e.g., less than 3 wt. %, less than 2 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst. In some embodiments, the metal loading of the precious metal may be less than the metal loadings of the cobalt and/or tin.

In some embodiments, catalyst may include a further second metal, i.e. promoter metal, selected from the group consisting of copper, iron, vanadium, nickel, titanium, zinc, chromium, molybdenum, tungsten, lanthanum, cerium, and manganese, any of the aforementioned precious metals, in particular rhenium, ruthenium, and gold, and combinations thereof. When present, the second metal loading may be from 0.01 to 10 wt. %, e.g., from 0.1 to 5 wt. %, or from 0.5 to 3 wt. %.

The total weight of all the metals, including the aforementioned precious metal, present in the catalyst preferably is from 0.1 to 30 wt. %, e.g., from 0.5 to 25 wt. %, or from 1.0 to 15 wt. %. In one embodiment, the catalyst may comprise from cobalt in an amount from 3 to 25 wt. % and tin in an amount from 0.05 to 4.5 wt. %, provided that the molar ratio of cobalt:tin is at least 11:1. The cobalt and/or tin for purposes of the present invention may be disposed on the modified support and may be part of the modified support. The total weight of the cobalt and/or tin may include the combined weight of the cobalt and/or tin in the modified support and the cobalt and/or tin disposed on the modified support. Thus, for example, the modified support may comprise from 0.1 to 15 wt. %, e.g. from 0.5 to 10 wt. %, of cobalt and/or tin and the cobalt and/or tin disposed on the modified support may be present in an amount from 0.1 to 15 wt. %, e.g., from 0.5 to 10 wt. %, provided that the total metal loading of the cobalt and/or tin is less than 30 wt. %. For purposes of the present specification, unless otherwise indicated, weight percent is based on the total weight the catalyst including metal and support.

Preferred metal combinations for some exemplary catalyst compositions include platinum/tin on a modified support comprising cobalt and tin, platinum/ruthenium on a modified support comprising cobalt and tin, platinum/rhenium on a modified support comprising cobalt and tin, platinum/cobalt on a modified support comprising tin and platinum/tin on a modified support comprising cobalt. In some embodiments, the catalyst comprises at least three metals on a support, e.g., one precious metal, cobalt and tin. Exemplary combinations may include platinum/cobalt/tin, platinum/cobalt/tin on a modified support comprising cobalt and tin, and palladium/cobalt/tin on a modified support comprising cobalt and tin. Each of the modified support also may comprise a suitable a support modifier metal selected from the group consisting of tungsten, molybdenum, vanadium, niobium, and tantalum.

The catalysts of the present invention comprise a suitable support material, preferably a modified support. In one embodiment, the support material may be an inorganic oxide. The support material may be selected from the group consisting of silica, alumina, titania, silica/alumina, pyrogenic silica, high purity silica, zirconia, carbon (e.g., carbon black or activated carbon), zeolites and mixtures thereof. Preferably, the support material comprises a silicaceous support material such as silica, pyrogenic silica, or high purity silica. In one embodiment the silicaceous support material is substantially free of alkaline earth metals, such as magnesium and calcium. The support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a silicaceous support material, e.g., silica, having a surface area of at least 50 m$^2$/g, e.g., at least 100 m$^2$/g, or at least 150 m$^2$/g. In terms of ranges, the silicaceous support material preferably has a surface area from 50 to 600 m$^2$/g, e.g., from 100 to 500 m$^2$/g or from 100 to 300 m$^2$/g. High surface area silica, as used throughout the application, refers to silica having a surface area of at least 250 m$^2$/g. For purposes of the present specification, surface area refers to BET nitrogen surface area, meaning the surface area as determined by ASTM D6556-04, the entirety of which is incorporated herein by reference.

The preferred silicaceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 cm$^3$/g, e.g., from 0.7 to 1.5 cm$^3$/g or from 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density from 0.1 to 1.0 g/cm$^3$, e.g., from 0.2 to 0.9 g/cm$^3$ or from 0.3 to 0.8 g/cm$^3$. In teems of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the cobalt and/or tin that are disposed on the support are generally in the foam of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. In one embodiment, the support modifier comprises metal selected from the group consisting of tungsten, molybdenum, vanadium, niobium, and tantalum.

In one embodiment, the acidic modifier may also include those selected from the group consisting of $WO_3$, $MoO_3$, $V_2O_5$, $VO_2$, $V_2O_3$, $Nb_2O_5$, and $Ta_2O_5$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $Mo_9O_{26}$, $Mo_8O_{23}$, $Mo_5O_{14}$, $Mo_{17}O_{47}$, $Mo_4O_{11}$, or $MoO_2$. In one embodiment, the tungsten oxide may be cubic tungsten oxide ($H_{0.5}WO_3$). It has now surprisingly and unexpectedly been discovered that the use of such metal oxide support modifiers in combination with a precious metal and cobalt and/or tin may result in catalysts having multifunctionality, and which may be suitable for converting a carboxylic acid, such as acetic acid, as well as corresponding esters thereof, e.g., ethyl acetate, to one or more hydrogenation products, such as ethanol, under hydrogenation conditions.

In some embodiments, the acidic support modifier comprises a mixed metal oxide comprising at least one of the cobalt and/or tin and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and/or manganese tantalate. In one embodiment, the catalyst does not comprise tin tungstate and is substantially free of tin tungstate. It has now been discovered that catalysts containing such mixed metal support modifiers may provide the desired degree of multifunctionality at increased conversion, e.g., increased ester conversion, and with reduced byproduct formation, e.g., reduced diethyl ether formation.

In one embodiment, the catalyst comprises from 0.25 to 1.25 wt. % platinum, from 1 to 10 wt. % cobalt, and from 1 to 10 wt. % tin on a silica or a silica-alumina support material. The cobalt and tin may be disposed on the support material and may be part of the modified support. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %.

The reduced tin loading may further reduce the formation of tin tungstate. Without being by bound theory, it is believed that the presence of tin tungstate on the modified support or catalyst tends to decrease catalytic activity in the conversion of acetic acid to ethanol. When used on the modified support, tin does contribute to improved catalytic activity and catalyst lifetime. However, when tin is present with tungsten, the undesirable tin tungstate species may form. To prevent the formation of tin tungstate, it has been found the use of cobalt may inhibit the formation of tin tungstate. This allows the preferential formation of cobalt tungstate over tin tungstate. In addition, this allows the use of tin on the modified support to thus maintain sufficient catalyst activity and catalyst lifetime. In one embodiment, the modified support comprises cobalt tungstate and tin, but the modified support is substantially free of tin tungstate.

Processes for Making the Catalyst

The present invention also relates to processes for making the catalyst. Without being bound by theory, the process for making the catalyst may improve one or more of acetic acid conversion, ester conversion, ethanol selectivity and overall productivity. In one embodiment, the support is modified with one or more support modifiers and the resulting modified support is subsequently impregnated with a precious metal and cobalt and/or tin to form the catalyst composition. For example, the support may be impregnated with a support modifier solution comprising a support modifier precursor and optionally one or more cobalt and/or tin precursors to form the modified support. After drying and calcination, the resulting modified support is impregnated with a second solution comprising precious metal precursor and optionally one or more of the cobalt and/or tin precursors, followed by drying and calcination to form the final catalyst.

In this embodiment, the support modifier solution may comprise a support modifier metal precursor and one or more cobalt and/or tin precursors, more preferably at least two cobalt and/or tin precursors. The precursors preferably are comprised of salts of the respective metals in solution, which, when heated, are converted to elemental metallic form or to a metal oxide. Cobalt and/or tin precursors are impregnated onto the support material simultaneously and/or sequentially with the support modifier precursor, and cobalt and/or tin may interact with the support modifier metal at a molecular metal upon formation to form one or more polymetallic crystalline species, such as cobalt tungstate. In other embodiments, cobalt and/or tin will not interact with the support modifier metal precursor and are separately deposited on the support material, e.g., as discrete metal nanoparticles or as an amorphous metal mixture. Thus, the support material may be modified with one or more cobalt and/or tin precursors at the same time that it is modified with a support modifier metal, and cobalt and/or tin may or may not interact with the support modifier metal to form one or more polymetallic crystalline species.

In some embodiments, the support modifier may be added as particles to the support material. For example, one or more support modifier precursors, if desired, may be added to the support material by mixing the support modifier particles with the support material, preferably in water. When mixed it is preferred for some support modifiers to use a powdered material of the support modifiers. If a powdered material is employed, the support modifier may be pelletized, crushed and sieved prior to being added to the support.

As indicated, in most embodiments, the support modifier preferably is added through a wet impregnation step. Preferably, a support modifier precursor to the support modifier may be used. Some exemplary support modifier precursors include alkali metal oxides, alkaline earth metal oxides, Group IIB metal oxides, Group MB metal oxides, Group IVB metal oxides, Group VB metal oxides, Group VIB metal oxides, Group VIIB metal oxides, and/or Group VIII metal oxides, as well as preferably aqueous salts thereof.

Although the overwhelming majority of metal oxides and polyoxoion salts are insoluble, or have a poorly defined or limited solution chemistry, the class of isopoly- and heteropolyoxoanions of the early transition elements forms an important exception. These complexes may be represented by the general formulae:

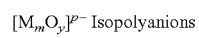

$[M_mO_y]^{p-}$ Isopolyanions

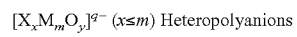

$[X_xM_mO_y]^{q-}$ ($x \leq m$) Heteropolyanions where M is selected from tungsten, molybdenum, vanadium, niobium, tantalum and mixtures thereof, in their highest ($d^0$, $d^1$) oxidations states. Such polyoxometalate anions form a structurally distinct class of complexes based predominately, although not exclusively, upon quasi-octahedrally-coordinated metal atoms. The elements that can function as the addenda atoms, M, in heteropoly- or isopolyanions may be limited to those with both a favorable combination of ionic radius and charge and the ability to form $d_\pi$-$p_\pi$ M-O bonds. There is little restriction, however, on the heteroatom, X, which may be selected from virtually any element other than the rare gases. See, e.g., M. T. Pope, *Heteropoly and Isopoly Oxometalates*, Springer Verlag, Berlin, 1983, 180; Chapt. 38, *Comprehensive Coordination Chemistry*, Vol. 3, 1028-58, Pergamon Press, Oxford, 1987, the entireties of which are incorporated herein by reference.

Polyoxometalates (POMs) and their corresponding heteropoly acids (HPAs) have several advantages making them economically and environmentally attractive. First, HPAs have a very strong approaching the superacid region, Bronsted acidity. In addition, they are efficient oxidants exhibiting fast reversible multielectron redox transformations under rather mild conditions. Solid HPAs also possess a discrete ionic structure, comprising fairly mobile basic structural units, e.g., heteropolyanions and countercations ($H^+$, $H_3O^+$, $H_5O_2^+$, etc.), unlike zeolites and metal oxides.

In view of the foregoing, in some embodiments, the support modifier precursor comprises a POM, which preferably comprises a metal selected from the group consisting of tungsten, molybdenum, niobium, vanadium and tantalum. In some embodiments, the POM comprises a hetero-POM. A non-limiting list of suitable POMs includes phosphotungstic acid ($H-PW_{12}$) ($H_3PW_{12}O_{40} \cdot nH_2O$), ammonium metatungstate (AMT) (($NH_4)_6H_2W_{12}O_{40} \cdot H_2O$), ammonium heptamolybdate tetrahydrate, (AHM) (($NH_4)_6Mo_7O_{24} \cdot 4H_2O$), silicotungstic acid hydrate ($H-SiW_{12}$) ($H_4SiW_{12}O_{40} \cdot H_2O$), silicomolybdic acid ($H-SiMo_{12}$) ($H_4SiMo_{12}O_{40} \cdot nH_2O$), and phosphomolybdic acid ($H-PMo_{12}$) ($H_3PMo_{12}O_{40} \cdot nH_2O$).

The use of POM-derived support modifiers in the catalyst compositions of the invention has now surprising and unexpectedly been shown to provide bi- or multi-functional catalyst functionality, desirably resulting in conversions for both acetic acid and byproduct esters such as ethyl acetate, thereby rendering them suitable for catalyzing mixed feeds comprising, for example, acetic acid and ethyl acetate.

Impregnation of the precious metal, cobalt and/or tin onto the support, e.g., modified support, may occur simultaneously (co-impregnation) or sequentially. In simultaneous impregnation, the two or more metal precursors are mixed together and added to the support, preferably modified support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the metal precursors in the event the precursors are incompatible with the desired solvent, e.g., water.

In sequential impregnation, the first metal precursor may be added to the modified support followed by drying and calcining, and the resulting material may then be impregnated with the remaining metal precursor each followed by an additional drying step and calcining step to form the final catalyst composition. Additional metal precursors may be added in a similar manner. Of course, combinations of sequential and simultaneous impregnation may be employed if desired.

In embodiments where the precious metal, cobalt and/or tin are applied to the catalyst in multiple sequential impregnation steps, the catalyst may be said to comprise a plurality of "theoretical layers." For example, where a first metal is impregnated onto a support followed by impregnation of a second metal, the resulting catalyst may be said to have a first theoretical layer comprising the first metal and a second theoretical layer comprising the second metal. As discussed above, in some aspects, more than one cobalt and/or tin precursor may be co-impregnated onto the support in a single step such that a theoretical layer may comprise more than one metal or metal oxide. In another aspect, the same metal precursor may be impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the catalyst support depending, for example, on the conditions employed in catalyst formation, on the amount of metal used in each step and on the specific metals employed.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, a support modifier precursor, and preferably one or more cobalt and/or tin precursors. The solution is stirred and combined with the support material using, for example, incipient wetness techniques in which the support modifier precursor is added to a support material having the same pore volume as the volume of the solution. Impregnation occurs by adding, optionally drop wise, a solution containing the precursors of either or both the support modifier metals, cobalt and/or tin, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 100° C. to 200° C. or about 120° C., for a period from 1 to 24 hours, e.g., from 3 to 15 hours or from 6 to 12 hours. The dried support may be calcined optionally with ramped heating, for example, at a temperature from 300° C. to 900° C., e.g., from 400° C. to 750° C., from 500° C. to 600° C. or at about 550° C., for a period of time from 1 to 12 hours, e.g., from 2 to 10 hours, from 4 to 8 hours or about 6 hours, to form the final modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified support and, ultimately, the final catalyst.

In one embodiment, the catalyst of the present invention may be prepared using a bulk catalyst technique. Bulk catalysts may be formed by precipitating precursors to support modifier metals, cobalt and/or tin. The precipitating may be controlled by changing the temperature, pressure, and/or pH. In some embodiments, the bulk catalyst preparation may use a binder. A support material may not be used in a bulk catalyst process. Once precipitated, the bulk catalyst may be shaped by spraying drying, pelleting, granulating, tablet pressing, beading, or pilling. Suitable bulk catalyst techniques may be used such as those described in Krijn P. de Jong, ed., Synthesis of Solid Catalysts, Wiley, (2009), pg. 308, the entire contents and disclosure of which is incorporated by reference.

In one embodiment, the precious metal, cobalt and/or tin are impregnated onto the support, preferably onto any of the above-described modified supports. A precursor of the precious metal preferably is used in the metal impregnation step, such as a water soluble compound or water dispersible compound/complex that includes the precious metal of interest. Similarly, one or more precursors to cobalt and/or tin may also be impregnated into the support, preferably modified support. Depending on the metal precursors employed, the use of a solvent, such as water, glacial acetic acid, nitric acid or an organic solvent, may be preferred to solubilize the metal precursors.

In one embodiment, separate solutions of the metal precursors are formed, which are subsequently blended prior to being impregnated on the support. For example, a first solution may be formed comprising a first metal precursor, and a second solution may be formed comprising a second metal precursor and optionally a third metal precursor. At least one of the first, second and optional third metal precursors preferably is a precious metal precursor, and the other(s) are preferably cobalt and/or tin precursors (which may or may not comprise precious metal precursors). Either or both solutions preferably comprise a solvent, such as water, glacial acetic acid, hydrochloric acid, nitric acid or an organic solvent.

In one exemplary embodiment, a first solution comprising a first metal halide is prepared. The first metal halide comprises a tin halide, e.g., a tin chloride such as tin (II) chloride and/or tin (IV) chloride. A second metal precursor, as a solid or as a separate solution, is combined with the first solution to form a combined solution. The second metal precursor comprises a cobalt oxalate, acetate, halide or nitrate. A second solution is also prepared comprising a precious metal precursor, such as a halide of rhodium, rhenium, ruthenium, platinum or palladium. The second solution is combined with the combined solution to form a mixed metal precursor solution. The resulting mixed metal precursor solution may then be added to the modified support, followed by drying and calcining to form the final catalyst composition as described above. The resulting catalyst may or may not be washed after the final calcination step. Due to the difficulty in solubilizing some precursors, it may be desired to reduce the pH of the first and/or second solutions, for example by employing an acid such as acetic acid, hydrochloric acid or nitric acid, e.g., 6 to 10 M $HNO_3$.

In another aspect, a first solution comprising a first metal oxalate is prepared, such as an oxalate of cobalt and/or tin. In this embodiment, the first solution preferably further comprises an acid such as acetic acid, hydrochloric acid, phosphoric acid or nitric acid, e.g., 6 to 10 M $HNO_3$. A second metal precursor, as a solid or as a separate solution, is combined with the first solution to form a combined solution. The second metal precursor, if used, preferably comprises cobalt oxalate, acetate, halide or nitrate. A second solution is also formed comprising a precious metal oxalate, for example, an oxalate of rhodium, rhenium, ruthenium, platinum or palladium, and optionally further comprises an acid such as acetic acid, hydrochloric acid, phosphoric acid or nitric acid, e.g., 6 to 10 M $HNO_3$. The second solution is combined with the combined solution to form a mixed metal precursor solution. The resulting mixed metal precursor solution may then be added to the modified support, followed by drying and calcining to form the final catalyst composition as described above. The resulting catalyst may or may not be washed after the final calcination step.

In one embodiment, the impregnated modified support is dried at a temperature from 100° C. to 140° C., from 110° C. to 130° C., or about 120° C., optionally from 1 to 12 hours, e.g., from 2 to 10 hours, from 4 to 8 hours or about 6 hours. If calcination is desired, it is preferred that the calcination temperature employed in this step is less than the calcination temperature employed in the formation of the modified support, discussed above. The second calcination step, for example, may be conducted at a temperature that is at least 50° C., at least 100° C., at least 150° C. or at least 200° C. less than the first calcination step, i.e., the calcination step used to form the modified support. For example, the impregnated catalyst may be calcined at a temperature from 200° C. to 500° C., from 300° C. to 400° C., or about 350° C., optionally for a period from 1 to 12 hours, e.g., from 2 to 10 hours, from 4 to 8 hours or about 6 hours.

In one embodiment, ammonium oxalate is used to solubilize at least one of the metal precursors, e.g., a tin precursor, as described in U.S. Pat. No. 8,211,821, the entirety of which is incorporated herein by reference. In this aspect, a solution of the second metal precursor may be made in the presence of ammonium oxalate as solubilizing agent, and the precious metal precursor may be added thereto, optionally as a solid or a separate solution. If used, the third metal precursor may be combined with the solution comprising the first precursor and tin oxalate precursor, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the modified support followed by drying and calcining to form the final catalyst composition as described above.

The specific precursors used in the various embodiments of the invention may vary widely. Suitable metal precursors may include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, $Pt(NH_3)_4(NO_4)_2$. Generally, both from the point of view of economics and environmental aspects, aqueous solutions of soluble compounds of platinum and palladium are preferred. In one embodiment, the precious metal precursor is not a metal halide and is substantially free of metal halides, while in other embodiments, as described above, the precious metal precursor is a halide.

In another example, cobalt and/or tin are co-impregnated with the tungsten precursor on the support material and may form a mixed oxide with $WO_3$, e.g., cobalt tungstate, followed by drying and calcination. The resulting modified support may be impregnated, preferably in a single impregnation step or multiple impregnation steps, with one or more of the precious metals, cobalt and/or tin followed by a second drying and calcination step. In this manner, cobalt tungstate may be formed on the modified support. Again, the temperature of the second calcining step preferably is less than the temperature of the first calcining step.

Use of Catalyst to Hydrogenate Acetic Acid and Ethyl Acetate

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

After the washing, drying and calcining of the catalyst is completed, the catalyst may be reduced in order to activate it. Reduction is carried out in the presence of a reducing gas, preferably hydrogen. The reducing gas is optionally continuously passed over the catalyst at an initial ambient temperature that is increased up to 400° C. In one embodiment, the reduction is carried out after the catalyst has been loaded into the reaction vessel where the hydrogenation will be carried out.

In one embodiment the invention is to a process for producing ethanol by hydrogenating a feed stream comprising compounds selected from acetic acid, ethyl acetate and mixtures thereof in the presence of any of the above-described catalysts. In some embodiments, the feed stream may comprise at least 5 wt. % ethyl acetate, e.g., at least 10 wt. % or at least 15 wt. %. One particular preferred reaction is to make ethanol from acetic acid. The hydrogenation reaction may be represented as follows:

$$HOAc + 2H_2 \rightarrow EtOH + H_2O$$

In some embodiments, the catalyst may be characterized as a bifunctional catalyst in that it effectively catalyzes the hydrogenation of acetic acid to ethanol as well as the conversion of ethyl acetate to one or more products, preferably ethanol.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C$:$^{12}C$ ratio of the methanol, acetic acid and/or ethanol may be from one half to about 1 of the $^{14}C$:$^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. The microorganism employed in the fermentation process may be *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, the feed stream comprises acetic acid and ethyl acetate. A suitable acetic acid feed stream comprises one or more of the compounds selected from the group consisting of acetic acid, acetic anhydride, acetaldehyde, ethyl acetate, diethyl acetal, diethyl ether, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of a carboxylic acid, e.g., acetic acid, to its corresponding alcohol, e.g., ethanol, and a second bifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1. For a mixed feed stream, the molar ratio of hydrogen to ethyl acetate may be greater than 5:1, e.g., greater than 10:1 or greater than 15:1.

Contact or residence time can also vary widely, depending upon such variables as amount of feed stream (acetic acid and/or ethyl acetate), catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, by employing the catalysts of the invention, the hydrogenation of acetic acid and/or ethyl acetate may achieve favorable conversion and favorable selectivity and productivity to ethanol in the reactor. For purposes of the present invention, the term "conversion" refers to the amount of acetic acid or ethyl acetate, whichever is specified, in the feed that is converted to a compound other than acetic acid or ethyl acetate, respectively. Conversion is expressed as a percentage based on acetic acid or ethyl acetate in the feed. The acetic acid conversion may be at least 75%, more preferably at least 80%, at least 90%, at least 95%, or at least 99%.

During the hydrogenation of acetic acid, ethyl acetate may be produced as a byproduct. Without consuming any ethyl acetate from the mixed vapor phase reactants, the conversion of ethyl acetate would be deemed negative. Some of the catalysts described herein are monofunctional in nature and are effective for converting acetic acid to ethanol, but not for converting ethyl acetate. The use of monofunctional catalysts may result in the undesirable build up of ethyl acetate in the system, particularly for systems employing one or more recycle streams that contain ethyl acetate to the reactor.

The preferred catalysts of the invention, however, are multifunctional in that they effectively catalyze the conversion of acetic acid to ethanol as well as the conversion of an alkyl acetate, such as ethyl acetate, to one or more products other than that alkyl acetate. The multifunctional catalyst is preferably effective for consuming ethyl acetate at a rate sufficiently great so as to at least offset the rate of ethyl acetate production, thereby resulting in a non-negative ethyl acetate conversion, i.e., no net increase in ethyl acetate is realized. The use of such catalysts may result, for example, in an ethyl acetate conversion that is greater than 5%.

In continuous processes, the ethyl acetate being added (e.g., recycled) to the hydrogenation reactor and ethyl acetate leaving the reactor in the crude product preferably approaches a certain level after the process reaches equilibrium. The use of a multifunctional catalyst that catalyzes the conversion of ethyl acetate as well as acetic acid results in a lower amount of ethyl acetate added to the reactor and less ethyl acetate produced relative to monofunctional catalysts. In preferred embodiments, the concentration of ethyl acetate in the mixed feed and crude product is less than 40 wt. %, less than 25 wt. % or less than 15 wt. %, after equilibrium has been achieved. In preferred embodiments, the process forms a crude product comprising ethanol and ethyl acetate, and the crude product has an ethyl acetate steady state concentration from 0.1 to 40 wt. %, e.g., from 0.1 to 20 wt. % or from 0.1 to 15 wt. %.

Although catalysts that have high acetic acid conversions are desirable, such as at least 75%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid and/or ethyl acetate. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the combined converted acetic acid and ethyl acetate. Preferably, total selectivity to ethanol is at least 60%, e.g., at least 70%, or at least 80%, at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. In some embodiments, when further water separation is used, the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

The following examples describe the catalyst and process of this invention.

EXAMPLES

Catalyst composition examples 1-18 comprise a platinum, cobalt, tin and tungsten. The catalyst compositions are reported in Table 2. The platinum weight percent is held constant while the cobalt, tin and tungsten are varied as shown in Table 2.

TABLE 2

CATALYST COMPOSITIONS

| Example | $WO_3$ (wt. %) | Co (wt. %) | Sn (wt. %) | Co:Sn Molar Ratio |
|---|---|---|---|---|
| 1 | 12 | 5.3 | 1.2 | 9:1 |
| 2 | 12 | 5.3 | 1.8 | 6:1 |
| 3 | 12 | 5.3 | 2.5 | 4:1 |
| 4 | 12 | 6.5 | 1.2 | 11:1 |
| 5 | 12 | 6.5 | 1.8 | 7:1 |
| 6 | 12 | 6.5 | 2.5 | 5:1 |
| 7 | 12 | 7.5 | 1.2 | 13:1 |
| 8 | 12 | 7.5 | 1.8 | 8:1 |
| 9 | 12 | 7.5 | 2.5 | 6:1 |
| 10 | 16 | 5.3 | 1.2 | 9:1 |
| 11 | 16 | 5.3 | 1.8 | 6:1 |
| 12 | 16 | 5.3 | 2.5 | 4:1 |
| 13 | 16 | 6.5 | 1.2 | 11:1 |
| 14 | 16 | 6.5 | 1.8 | 7:1 |
| 15 | 16 | 6.5 | 2.5 | 5:1 |
| 16 | 16 | 7.5 | 1.2 | 13:1 |
| 17 | 16 | 7.5 | 1.8 | 8:1 |
| 18 | 16 | 7.5 | 2.5 | 6:1 |

A feed stream comprising 15% ethyl acetate and 85% acetic acid was fed to a reactor comprising catalyst compositions according to examples 1-18. The acetic acid conversion and ethyl acetate conversion were measured. The results are reported in Table 3.

TABLE 3

ACETIC ACID AND ETHYL ACETATE CONVERSION (%)

| Example | Co:Sn Molar Ratio | HOAc Conversion (%) | EtOAc Conversion (%) |
|---|---|---|---|
| 1 | 9:1 | 97.87 | −1.00 |
| 2 | 6:1 | 98.03 | −7/65 |
| 3 | 4:1 | 83.95 | −7.57 |
| 4 | 11:1 | 93.85 | −14.20 |
| 5 | 7:1 | 97.84 | −6.94 |
| 6 | 5:1 | 84.40 | −6.57 |
| 7 | 13:1 | 77.87 | 13.96 |
| 8 | 8:1 | 98.54 | 3.23 |
| 9 | 6:1 | 98.47 | 2.93 |
| 10 | 9:1 | 98.46 | −1.18 |
| 11 | 6:1 | 97.80 | −15.69 |
| 12 | 4:1 | 97.90 | −16.24 |
| 13 | 11:1 | 98.53 | 5.24 |
| 14 | 7:1 | 98.47 | 0.59 |
| 15 | 5:1 | 97.88 | −13.58 |
| 16 | 13:1 | 98.57 | 5.26 |
| 17 | 8:1 | 97.78 | −9.49 |
| 18 | 6:1 | 98.33 | −3.44 |

Examples 7 and 16, which have a molar ratio of Co:Sn of greater than 11:1, demonstrated improved ethyl acetate conversions and high acetic acid conversion. Also Example 13 which had higher tungsten loading than Example 4 demonstrated an improved ethyl acetate conversion.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A catalyst on a modified support, comprising a precious metal, tin and cobalt, wherein the modified support comprises a support modifier metal selected from the group consisting of tungsten, molybdenum, vanadium, niobium, and tantalum; and further wherein a molar ratio of cobalt to tin is at least 11:1.

2. The catalyst of claim 1, wherein the precious metal is selected from the group consisting of rhodium, rhenium, ruthenium, platinum, palladium, osmium, iridium and gold.

3. The catalyst of claim 1, further comprising a second metal that is selected from the group consisting of copper, iron, vanadium, nickel, titanium, zinc, chromium, molybdenum, tungsten, lanthanum, cerium, and manganese.

4. The catalyst of claim 1, wherein the precious metal is present in an amount from 0.1 to 5 wt. %, the tin is present in an amount from 0.05 to 4.5 wt. % and the cobalt is present in an amount from 3 to 25 wt. %, based on the total weight of the catalyst.

5. The catalyst of claim 1, wherein the support modifier metal is tungsten.

6. The catalyst of claim 1, wherein the modified support further comprises cobalt, tin, or mixtures thereof.

7. The catalyst of claim 1, wherein there is an excess molar amount of tin compared to the precious metal.

8. The catalyst of claim 1, wherein the modified support comprises a support material selected from the group consisting of silica, alumina, titania, silica/alumina, pyrogenic silica, high purity silica, zirconia, carbon, zeolites and mixtures thereof.

9. A process for producing ethanol, comprising contacting a feedstock comprising acetic acid and hydrogen in a reactor at an elevated temperature in the presence of the catalyst of claim 1, under conditions effective to form ethanol.

10. The process of claim 9, wherein the feed stream further comprises ethyl acetate.

11. The process of claim 9, wherein the feed stream further comprises ethyl acetate and wherein ethyl acetate conversion is at least 5%.

12. The process of claim 9, wherein acetic acid conversion is at least 75%.

13. The process of claim 9, wherein acetic acid selectivity to ethanol is greater than 80%.

14. The process of claim 9, wherein the hydrogenation is performed in a vapor phase at a temperature of from 125° C. to 350° C., a pressure of 10 kPa to 3000 kPa, and a hydrogen to acetic acid molar ratio of greater than 4:1.

15. The process of claim 9, wherein the acetic acid is derived from a carbonaceous material selected from the group consisting of oil, coal, natural gas and biomass.

16. A catalyst on a modified support, comprising a precious metal and tin, wherein the modified support comprises cobalt and a support modifier metal selected from the group consisting of tungsten, molybdenum, vanadium, niobium, and tantalum; and further wherein the molar ratio of cobalt to tin is at least 11:1.

17. The catalyst of claim 16, wherein the precious metal is selected from the group consisting of rhodium, rhenium, ruthenium, platinum, palladium, osmium, iridium and gold.

18. The catalyst of claim 16, further comprising a second metal that is selected from the group consisting of copper, iron, vanadium, nickel, titanium, zinc, chromium, molybdenum, tungsten, lanthanum, cerium, and manganese.

19. A catalyst on a modified support, comprising a precious metal, tin and cobalt, wherein the modified support comprises cobalt, tin, and a support modifier metal selected from the group consisting of tungsten, molybdenum, vanadium, niobium, and tantalum; and further wherein the molar ratio of cobalt to tin is at least 11:1.

20. The catalyst of claim 19, wherein the precious metal is selected from the group consisting of rhodium, rhenium, ruthenium, platinum, palladium, osmium, iridium and gold.

\* \* \* \* \*